(12) United States Patent
Guo et al.

(10) Patent No.: US 9,912,926 B2
(45) Date of Patent: Mar. 6, 2018

(54) BIOCHEMISTRY MEASUREMENT DEVICE AND METHOD THEREOF

(71) Applicants: LITE-ON ELECTRONICS (GUANGZHOU) CO., LTD., Guangzhou (CN); LITE-ON TECHNOLOGY CORPORATION, Taipei (TW)

(72) Inventors: Hong Ru Guo, Tainan (TW); Yu Jin Kao, Zhubei (TW); Yang-Li Yang, Taichung (TW)

(73) Assignees: LITE-ON ELECTRONICS (GUANGZHOU) CO., LTD., Guangzhou (CN); LITE-ON TECHNOLOGY CORPORATION, Taipei (TW)

( * ) Notice: Subject to any disclaimer, the term of this patent is extended or adjusted under 35 U.S.C. 154(b) by 151 days.

(21) Appl. No.: 15/081,165

(22) Filed: Mar. 25, 2016

(65) Prior Publication Data

US 2017/0150113 A1   May 25, 2017

(30) Foreign Application Priority Data

Nov. 19, 2015  (TW) .............................. 104138195 A (51) Int. Cl.
| | | |
|---|---|---|
| G01N 33/50 | (2006.01) | |
| G01N 33/53 | (2006.01) | |
| H04N 9/67 | (2006.01) | |
| G01N 33/66 | (2006.01) | |
| G06T 7/00 | (2017.01) | |
| G06T 7/90 | (2017.01) | |
| H01L 27/146 | (2006.01) | |

(52) U.S. Cl.
CPC ............... *H04N 9/67* (2013.01); *G01N 33/66* (2013.01); *G06T 7/0016* (2013.01); *G06T 7/90* (2017.01); *G06T 2207/10016* (2013.01); *G06T 2207/10024* (2013.01); *G06T 2207/30072* (2013.01); *H01L 27/14645* (2013.01)

(58) Field of Classification Search
CPC .......... G01N 33/66; G06T 2207/10016; G06T 2207/10024; G06T 2207/30072; G06T 7/0016; G06T 7/90; H04N 9/67
See application file for complete search history.

(56) References Cited

U.S. PATENT DOCUMENTS

2013/0329053 A1* 12/2013 Jones .................... H04N 9/735
348/164

* cited by examiner

*Primary Examiner* — Jennifer Wecker
(74) *Attorney, Agent, or Firm* — K&L Gates LLP (57) ABSTRACT

A biochemistry measurement method includes obtaining a first pixel array and a second pixel array with a photosensitive array, transforming the first pixel array and the second pixel array into a first color space coordinate matrix and a second color space coordinate matrix, extracting the first color space coordinate matrix and the second color space coordinate matrix to from a third color space coordinate matrix and a fourth color space coordinate matrix, and obtaining a color space vector matrix according to the third color space coordinate matrix and the fourth color space coordinate matrix.

17 Claims, 6 Drawing Sheets

BIOCHEMISTRY MEASUREMENT DEVICE AND METHOD THEREOF

RELATED APPLICATIONS

This application claims the benefit of Taiwan Patent Application No. 104138195, filed on Nov. 19, 2015, at the Taiwan Intellectual Property Office, the entire disclosure of which is incorporated herein by reference.

FIELD OF THE INVENTION

The present invention relates to a biochemistry measurement device, specifically a biochemistry inspector and a biochemistry inspection method.

BACKGROUND OF THE INVENTION

The optical inspection is used in most of the current biochemistry measurement devices. In the optical inspection, an illuminant is used to produce the inspection light which turns into the transmitted light or the reflected light after irradiating to the test sample. The specific range (usually +/−10 nm of the specific wave length) of spectrum is extracted by the band pass filter and the optical signal of the specific range of spectrum is transformed into the electrical signal of the specific range of spectrum by the photodiode. The electrical signals of the test sample and the calibration sample obtained from the same specific range of spectrum are compared then. According to the difference in the comparison, the information of the test sample concentration can be calculated and obtained.

In the abovementioned optical inspection, all the possible error factors have to be controlled precisely, such as the error factors of the manufacturing processes of the illuminant, the photodiode and the band pass filter, or the error factors of the assembly of each part of the device. All these error factors may cause the inaccuracy of the measurement result.

In addition, the electrical signal produced by the photodiode is generated by the light irradiating to the PN junction of the photodiode. If the PN junction is not shaded by the test sample evenly, the electrical signal does not stand for the concentration of the test sample accurately.

SUMMARY OF THE INVENTION

To overcome the disadvantages, the present invention uses the photosensitive unit array to capture the transmitted light and/or the reflected light of the test sample. At the same time, the light information received by each photosensitive unit is grouped into the different groups with the intensity information in different colors, such as grouped with RGB color model. The received intensity information in different colors is mapped into RGB color space, and therefore the light information can be transformed into the color space coordinate matrix that is the spatialized image information.

In accordance with an aspect of the present invention, a biochemistry inspector is provided. The biochemistry inspector includes an illuminant, a sample well, a photosensitive unit array and an image processor. The illuminant generates a light. The sample well contains a sample for receiving the light and generating an image. The photosensitive unit array receives and transforms the image into a pixel array and the image processor receives and transforms the pixel array into a first color space coordinate matrix, and extracts a second color space coordinate matrix from the first color space coordinate matrix according to a predetermined color space coordinate threshold.

Preferably, the image processor obtains a color space vector matrix based on a predetermined color space coordinate matrix and the second color space coordinate matrix.

Preferably, the image processor obtains a sample concentration matrix based on the color space vector matrix.

Preferably, the illuminant is a broadband light source.

Preferably, the illuminant is a white light source.

Preferably, the image is composed of a transmitted light of the sample.

Preferably, the image is composed of a reflected light of the sample.

Preferably, the biochemistry inspector further comprises an auxiliary photodiode coupled to the image processor for receiving a transmitted light of the sample and generating an electrical signal which is received and transformed into an assistant color space coordinate scalar by the image processor.

Preferably, the biochemistry inspector further comprises an auxiliary photosensitive unit array coupled to the image processor for receiving a transmitted light of the sample and generating an initial color space coordinate matrix which is received and transformed into an assistant color space coordinate matrix by the image processor.

In accordance with another aspect of the present invention, another biochemistry inspector is provided. The biochemistry inspector includes an illuminant, a sample well, a photosensitive unit array and an image processor. The illuminant generates a light. The sample well having a reagent contains a sample and receives the light for generating a first image, wherein a color reaction of the sample and the reagent is performed for a specific period of time to produce a second image. The photosensitive unit array receives and transforms the first image and the second image into a first pixel array and a second pixel array. The image processor receives the first pixel array and the second pixel array for transforming the first pixel array and the second pixel array respectively into a first color space coordinate matrix and a second color space coordinate matrix. The image processor extracts a third color space coordinate matrix from the first color space coordinate matrix according to a predetermined color space coordinate threshold and extracts a fourth color space coordinate matrix from the second color space coordinate matrix according to the predetermined color space coordinate threshold for obtaining a color space vector matrix from the third color space coordinate matrix and the fourth color space coordinate matrix.

Preferably, the image processor extracts an effective color space vector matrix from the color space vector matrix according to a predetermined color space vector.

Preferably, the image processor transforms the color space vector matrix into a color space scalar matrix, extracts an effective color space scalar matrix from the color space scalar matrix according to a predetermined color space scalar, and obtains an effective sample concentration matrix according to the effective color space scalar matrix.

In accordance with further aspect of the present invention, a biochemistry inspection method is provided. The biochemistry inspection method includes: obtaining a first pixel array and a second pixel array by a photosensitive unit array; transforming the first pixel array and the second pixel array respectively into a first color space coordinate matrix and a second color space coordinate matrix; extracting a third color space coordinate matrix and a fourth color space coordinate matrix respectively from the first color space coordinate matrix and the second color space coordinate matrix according to a predetermined color space coordinate matrix; and obtaining a color space vector matrix from the third color space coordinate matrix and the fourth color space coordinate matrix.

Preferably, the first pixel array is produced by a calibration sample image and the second pixel array is produced by a test sample image.

Preferably, the biochemistry inspection method further comprises obtaining a sample concentration matrix based on the color space vector matrix.

Preferably, the first pixel array is produced by a test sample image and the second pixel array is produced by a test sample image after a predetermined period of time.

Preferably, the biochemistry inspection method further comprises extracting an effective color space vector matrix from the color space vector matrix according to a predetermined color space vector; and obtaining an effective sample concentration matrix based on the effective color space vector matrix.

The present invention can select and pick out the effective spatialized image information from the acquired spatialized image information to prevent the error caused by the uneven transmitted or reflected light of the uneven test sample absorbed by the photosensitive surface of the photodiode. Furthermore, the image analysis process provided in this invention can suppress the errors coming from manufacturing process and assembling, improve the test accuracy, increase the yield of the biochemistry inspector and decrease the cost.

BRIEF DESCRIPTION OF THE DRAWINGS

The above objects and advantages of the present invention will become more readily apparent to those ordinarily skilled in the art after reviewing the following detailed descriptions and accompanying drawings, in which.

DETAILED DESCRIPTION OF THE PREFERRED EMBODIMENTS

Figure 1:
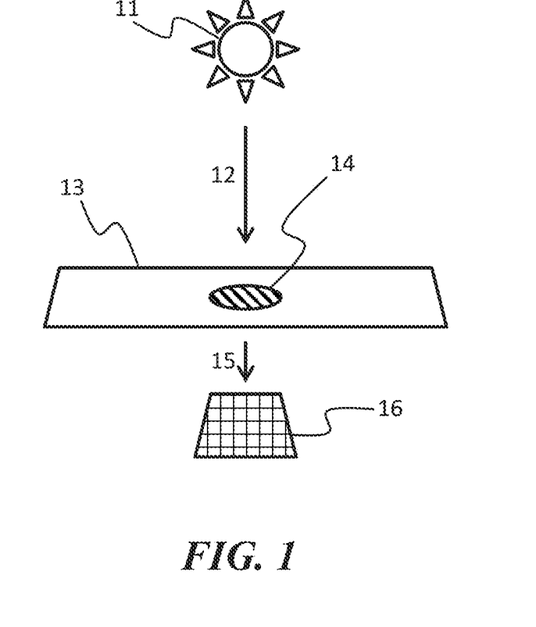
FIG. 1 is the diagram of the configuration of one of the embodiments.

The present invention provides a biochemistry inspector and one configuration of its embodiments is shown as FIG. 1. The illuminant 11 emits an incident light 12 to the test sample in the transparent sample well 14. The illuminant 11 can be a broadband light source or a white light source. After the incident light 12 penetrates the test sample, the produced transmitted light 15 is acquired by the photosensitive unit array 16 under the test slide 13 so as to produce the pixel array corresponding to the test sample. The image processor (not shown) receives the pixel array and performs the subsequent processing of the pixel array.

Figure 2:
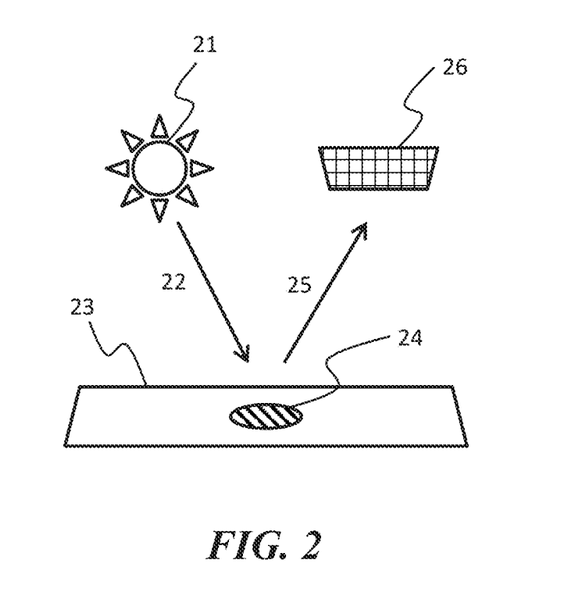
FIG. 2 is the diagram of the configuration of another embodiment.

The configuration of another embodiment is shown as FIG. 2, wherein the illuminant 21, the incident light 22, the test slide 23 and the transparent sample well 24 are the same as the illuminant 11, the incident light 12, the test slide 13 and the transparent sample well 14 shown in FIG. 1. The difference between FIGS. 1 and 2 is the position of the photosensitive unit array 26. In FIG. 2, the photosensitive unit array 26 receives the reflected light 25 of the test sample rather than the transmitted light 15 of the test sample shown in FIG. 1. Similarly, the image processor performs the subsequent processing of the pixel array.

Both of the charge-coupled device (CCD) imager and the complementary metal-oxide semiconductor (CMOS) imager can be used to implement the abovementioned photosensitive unit array, and both of them are integrated circuits. The manufacturing process of the integrated circuit has reliable yield currently. And thanks to the progress of the manufacturing process, each photosensitive surface of the photosensitive unit in the CCD/CMOS imager can be made in the extremely tiny scale.

Because the photosensitive unit array is made of the tiny photosensitive units, the photosensitive unit array is able to segment the area shaded by small amount of the test sample into a pixel array of the image of the test sample for the subsequent extraction and image processing. Therefore, it is effective to reduce the errors and the inaccuracy by using the photosensitive unit array as the device of the optical to electrical signal conversion.

Based on the current manufacturing process, for the CCD imager or the CMOS imager, each photosensitive unit can at least produce the electrical signals according to the absorption intensities of the red, green and blue lights at the same time. Therefore, the absorbed light in each pixel of the pixel array produced by the photosensitive unit array can be represented as "intensity$_{x,y}$=(r, g, b)$_{x,y}$", wherein the suffixed x and y stand for the row-column position of the pixel corresponding to photosensitive unit in the photosensitive unit array, and the r, g and b stand for the absorption intensities of the red, green and blue lights respectively. However, it should be noted that, it is almost impossible to absorb the light with single wavelength with the current technology. Strictly speaking, the absorption intensity of red light refers to the absorption intensity of the spectrum range which takes 640 nm as the center and covers the range of 640+/−Δλ nm. It is similar to the green and blue lights. The centers and the Δλs of the different colors are determined by the manufacturing process of the color filters in the photosensitive unit array respectively.

Therefore, photosensitive unit array can present the image of the sample well in the form of a pixel array. We take a 3×3 pixel array as an example:

$$\text{Image}_{3\times 3} = \begin{matrix} (r_{11}, g_{11}, b_{11})_{11} & (r_{12}, g_{12}, b_{12})_{12} & (r_{13}, g_{13}, b_{13})_{13} \\ (r_{21}, g_{21}, b_{21})_{21} & (r_{22}, g_{22}, b_{22})_{22} & (r_{23}, g_{23}, b_{23})_{23} \\ (r_{31}, g_{31}, b_{31})_{31} & (r_{32}, g_{32}, b_{32})_{32} & (r_{33}, g_{33}, b_{33})_{33} \end{matrix}$$

Figure 3:
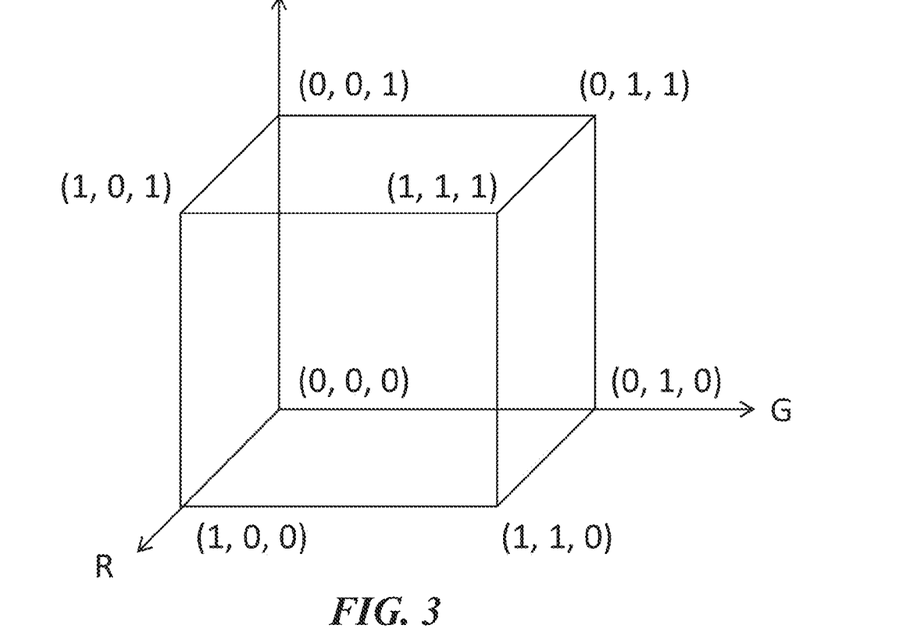
FIG. 3 is the diagram of the RGB color space.

After the pixel array is sent to the image processor, each $(r, g, b)_{x,y}$ is mapped into a color space respectively. Referring to FIG. 3, one common RGB color space is used as a demonstration here, in which the R axis stands for the intensity of red light, the G axis stands for the intensity of green light and the B axis stands for the intensity of blue light. According to the definition of chromatology, (0, 0, 0) is black, (0, 0, 1) is blue, (1, 0, 0) is red, (0, 1, 0) is green, (1, 1, 0) is yellow, (1, 0, 1) is magenta, (0, 1, 1) is cyan and (1, 1, 1) is white. Based on the abovementioned 3×3 pixel array, it can be represented as the form of 9 points in the RGB color space. However, according to the resolution of each photosensitive unit in the photosensitive unit array, the maximum distance from the origin is not limited to 1 in the practical applied RGB color space. Taking 8 bit resolution as an example, the maximum distance from the origin is 2 to the power of 8, i.e. 256. In this condition, (0, 0, 0) is black, (0, 0, 256) is blue, (256, 0, 0) is red and so on. It should be noted that the use of RGB color space is just one of the embodiments of the present invention and the CIELUV color space or the CIE 1964U*V*W* color space also can be used to achieve a similar function.

When the total volume of the test sample is not enough, one practicable approach is to dilute the test sample to satisfy with the minimum volume for the test, and to inversely derive the original properties of the test sample before the dilution from the diluted test sample. However, the optical properties of any given material are not always linearly related to the concentration or the reaction speed of the material, and therefore the result from the inversely derivation is not accurate.

Figure 4:
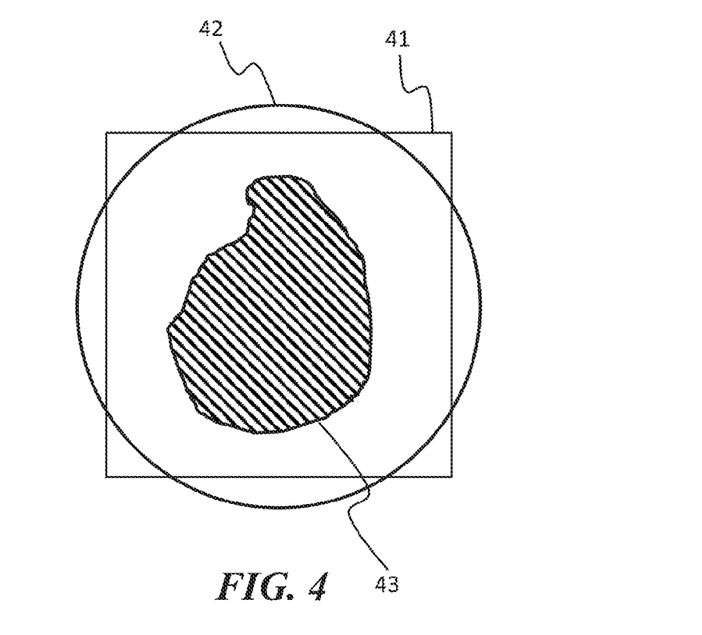
FIG. 4 is the diagram of the condition when the test sample without sufficient volume is applied to the prior art inspector.

Referring to FIG. 4, this is the stereotype that the volume of test sample 43 is not enough to shade or fill the entire transparent sample well 42. Because the electrical signal produced by the photodiode is based on the total intensity of the light irradiating on the photosensitive surface 41. Thus, once the volume of test sample 43 is not enough, the produced electrical signal is not able to consistent with the reality condition.

Figure 5:
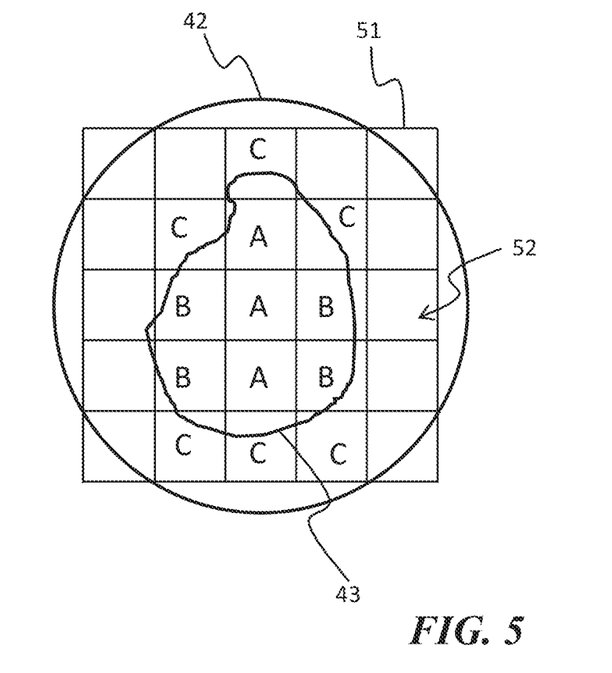
FIG. 5 is the diagram of the condition when the test sample without sufficient volume is applied to the present invention.

Referring to FIG. 5, the photosensitive unit array 51 is made of several photosensitive units 52. In this embodiment, one 5×5 pixel array is produced, and after the image processor receives the pixel array, it can be transformed into a color space coordinate matrix. The received total intensity of light of each photosensitive unit 52 is read, and a predetermined color space coordinate threshold is generated by the statics approach according to the received total light intensity of each photosensitive unit 52. The color space coordinate acquired from the areas unshaded by the test sample 43, the color space coordinate acquired from the areas partially shaded C by the test sample 43 and even the color space coordinate acquired from the areas insufficiently shaded B by the test sample 43 are ruled out based on the predetermined color space coordinate threshold. Only the areas fully shaded A are selected for the subsequent inspection to increase the accuracy.

In another embodiment of the present invention, the predetermined color space coordinate threshold can be implemented as a closed space in the color space to extract the color space coordinates from certain color range for the subsequent inspection. This setting about the predetermined color space coordinate threshold is helpful to rule out the pixels resulted from the particles of the precipitant and increase the accuracy when the test sample may produce certain precipitant.

In another embodiment of the present invention, when mass batch inspection is performed, some reagent which reacts with the test sample and causes the test sample change in color is coated on the surface of the sample well preliminarily. After the test sample is injected, some properties of the test sample are determined according to the level of the change in color of the test sample.

Figure 6:
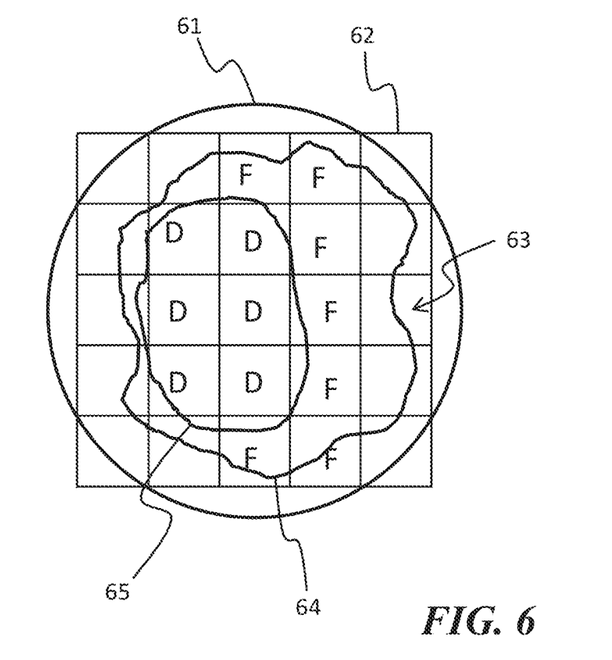
FIG. 6 is the diagram of the condition when the test sample in uneven thickness is applied to the present invention.

Referring to FIG. 6, the sample well 61 is coated with the reagent in color X. The test sample in color Y will become deep red when reacting with the reagent. The photosensitive unit array 62 and the photosensitive units 63 are the same as the photosensitive unit array 51 and the photosensitive units 52 shown in FIG. 5. When the total amount of the test sample is not enough, only partial test sample in the sample well has the sufficient thickness for the inspection due to the surface tension or the cohesive force, such as the test sample in the areas 65. These areas 65 shade the photosensitive units D. The edge of the test sample, such as the test sample in the areas 64, is not qualified for the required thickness to be inspected. These areas 64 shade some parts of the photosensitive unit array 62, such as the photosensitive units F. Thus, changed color of the color reaction in the areas 65 is accurate. The present invention can obtain the color space coordinates produced by the photosensitive units D corresponding to areas 65 either through the abovementioned approach or through the approach of the differences in color.

When the reaction starts, the color Y can be defined as a coordinate in a color space. Taking the RGB color space as an example, the coordinate is noted as $(r_Y, g_Y, b_Y)$, deep red is noted as $(r_{DR}, g_{DR}, b_{DR})$, and therefore the differences in color, $\Delta C$, can be noted as $(r_{DR}-r_Y, g_{DR}-g_Y, b_{DR}-b_Y)$. The $\Delta C$ can be represented as the form of vector, and can be transformed to the form of scalar.

After the color space coordinates in the start and end of the reaction are acquired, the color space vector matrix of the whole sample well can be obtained. The $\Delta C$ can be used as a threshold to extract the effective color space vector matrix produced by the photosensitive units D or the photosensitive units F from the color space coordinate matrix of the whole sample well. The image processor can transform the color space vector matrix into a color space scalar matrix and extracts an effective color space scalar matrix from the color space scalar matrix according to a predetermined color space scalar. An effective sample concentration matrix according to the effective color space scalar matrix can be obtained.

Even in the condition that no reaction is necessary, the inspector still has to be calibrated before the inspection starts. The calibration sample also produces a color space coordinate. After obtaining the color space coordinate of the test sample, the color space vector matrix standing for the absorption intensity of the test sample in the areas of each photosensitive unit can be acquired through the color space coordinates of the calibration sample and the test sample. In the condition that reaction is needed, the effective color space vector matrix can be acquired after a predetermined reaction time. The effective color space vector matrix can be used to calculate the reaction speed between the test sample and the reagent or the concentration of the test sample in the areas of each photosensitive unit.

Generally speaking, the Beer-Lambert law is adopted when the optical inspection for the material concentration is conducted. The Beer-Lambert law is defined as:

$$A = -\log_{10}\frac{I_t}{I_o} = \log_{10}\frac{1}{T} = K \cdot l \cdot c \qquad (1)$$

wherein A is the absorbance, $I_0$ is the intensity of the incident light, $I_t$ is the intensity of the transmitted light, T is the transmittance of the test sample, K is the extinction coefficient or the molar absorptivity of the test sample, l is the length of the light path in the light-absorbing material and c is the concentration of the light-absorbing material (g/L or mol/L).

The concept of the Beer-Lambert law is that the light passes through a solution containing the light-absorbing material. The intensity of the transmitted light is directly proportional to the concentration of the material and inversely proportional to the length of the light path which the light passes through, and therefore it can be expressed as:

$$I_t = I_0 \cdot K \cdot l \cdot (\text{concentration of the light-absorbing material}) \qquad (2)$$

Because it is almost impossible to absorb the light of single wavelength, actually each of $I_t$ and $I_0$ is the intensity in the spectrum range of $\lambda +/- \Delta\lambda$ nm and the length of the light path can be adjusted through the change in the thickness of the test sample to simplify Equation (2). Therefore, Equation (2) can be expressed as:

$$(\text{concentration of the light-absorbing material}) = K' \cdot I_{(\lambda+/-\Delta\lambda)} \qquad (3)$$

wherein $I_{(\lambda+/-\Delta\lambda)}$ is the intensity ratio of the transmitted light to the incident light in the light-absorbing material and is equal to $I_t/I_0$. K' is 1/K in the condition of light transmission, and it should be modified with a factor in the condition of light reflection.

Figure 7:
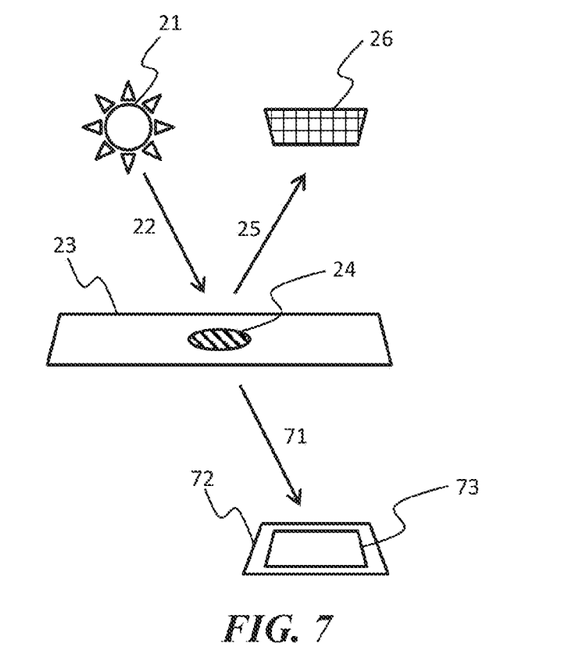
FIG. 7 is the configuration diagram of one of the embodiments which has a photodiode.

The present invention provides another approach to produce the threshold in one further embodiment except for producing the threshold based on the color space vector matrix as mentioned above. Referring to FIG. 7, under the configuration that the photosensitive unit array 26 receives the reflected light 25 of the test sample, one photodiode 72 is installed additionally to receive the transmitted light 71. The produced electrical signal when the light irradiates on the photosensitive surface 73 of the photodiode 72 is sent to the image processor. With the change of the test sample, the relative intensity of the reflected light and the transmitted light is going to alter. Therefore, when calibrating with the calibration sample, the image processor transforms the electrical signal into a scalar corresponding to the intensity of the light received by the photodiode 72 and multiplies the scalar with a factor to make it accord with the intensity of the light received by the photosensitive unit array 26 so as to generate an assistant color space coordinate scalar. Because the assistant color space coordinate scalar stands for the chromatology properties of the calibration sample, the assistant color space coordinate scalar can be used as a threshold to rule out the color space coordinates corresponding to the areas unshaded by test sample from the color space coordinate matrix produced by the whole sample well. The purpose to measure the areas shaded by the test sample can be achieved with this approach.

Figure 8:
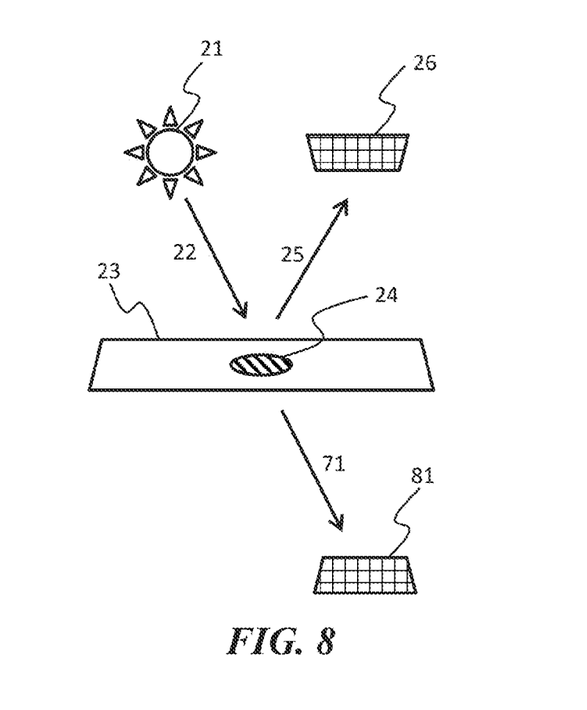
FIG. 8 is the configuration diagram of one of the embodiments which has an auxiliary photosensitive unit array.

Referring to FIG. 8, furthermore, the photodiode 72 in the previous embodiment can be replaced by an auxiliary photosensitive unit array 81. An initial color space coordinate matrix is obtained through the calibration with the calibration sample. The intensities from the auxiliary photosensitive unit array 81 and the photosensitive unit array 26 are used to generate an assistant color space coordinate matrix. Thus, the synchronization of the absorption intensities between the two photosensitive unit arrays is completed. This configuration is not for extracting the different thresholds, but for the real time measurement. The photosensitive unit array 26 detects the change in color of the sample well 24, and the auxiliary photosensitive unit array 81 inspects the addition or reduction of the concentration of certain specific material in the test sample corresponding to the change in color reaction. To the same reaction, this embodiment realizes the real time inspection to the reduction of the reactant and the addition of the product. That makes users be able to study the on-going reaction more thoroughly.

In the present invention, each of the incident intensities ($I_0$) for the photosensitive units can be obtained through the direct irradiation of the illuminant upon the photosensitive unit array. The absorbance of the test sample in the areas of each photosensitive unit can be acquired from the color space vector matrix or the effective color space vector matrix as abovementioned. By Equation (3), the sample concentration matrix or the effective sample concentration matrix of the test sample corresponding to the test sample in the areas of the photosensitive unit array can be calculated.

Figure 9A:
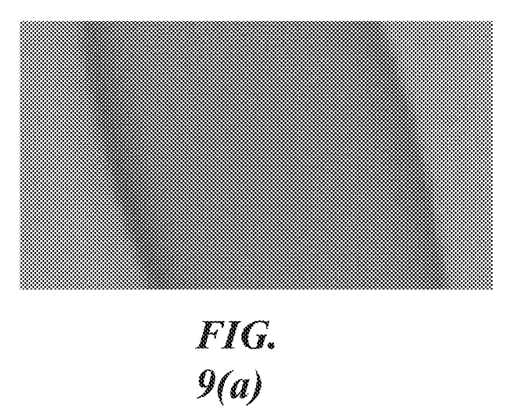
FIG. 9(a) is the image of the transparent sample well of the present invention acquired by the photosensitive unit array, wherein the transparent sample well is coated with the reagent to perform the color reaction with the blood sugar.
Figure 9B:
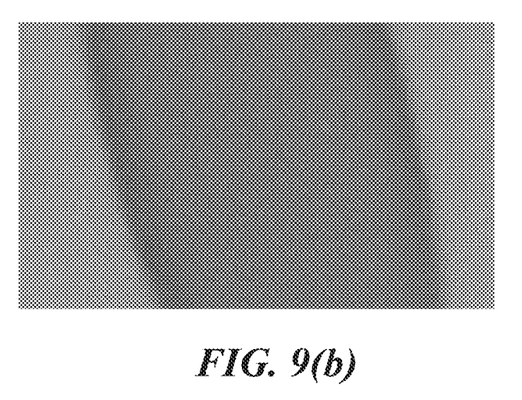
FIG. 9(b) is the image of the abovementioned transparent sample well filled with the test sample as the initiation of the color reaction.
Figure 9C:
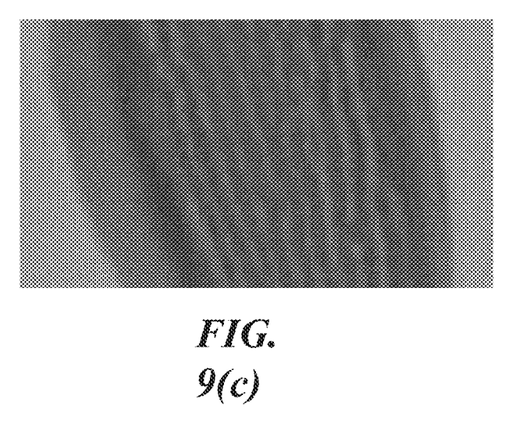
FIG. 9(c) is the image of the abovementioned color reaction which already enters the stationary phase.

The following is the implement course to measure the blood sugar with the approach of the difference in color. FIG. 9(a) is the image of the sample well of the present invention, wherein the sample well coated with the reagent can react with blood sugar to cause the color reaction, and therefore it appears as pale-yellow. After the test blood is centrifuged, the plasma is taken as the test sample to be injected into the sample well. As shown in FIG. 9(b), the color reaction starts immediately after the test sample is injected. The central part of the sample well is getting dark from pale-yellow, and the image processor records the images acquired by the photosensitive unit array every 2 seconds. FIG. 9(c) is the image of the sample well after 20 seconds from the reaction starts, and it can be observed that the result of the color reaction is not homogeneous. After the extraction, the record and calculation are performed and optimized to the effective areas of the image, and the result is shown as following Table 1.

TABLE 1

| time (second) | red light intensity (R) | green light intensity (G) | blue light intensity (B) | difference in color ($\Delta C$) |
|---|---|---|---|---|
| 0 (reaction start) | 157 | 162 | 118 | 0 |
| +2 | 132 | 134 | 111 | 38.184 |
| +4 | 98 | 95 | 101 | 90.879 |
| +6 | 86 | 80 | 95 | 110.878 |
| +8 | 77 | 72 | 91 | 123.406 |
| +10 | 74 | 66 | 90 | 129.958 |
| +12 | 68 | 61 | 87 | 138.141 |
| +14 | 67 | 58 | 85 | 141.439 |
| +16 | 63 | 54 | 84 | 147.160 |
| +18 | 63 | 53 | 83 | 148.128 |
| +20 | 61 | 53 | 81 | 149.887 |

In Table 1, all the recoded values of the intensities of red light, green light and blue light are the average of the intensities respectively from the photosensitive units located in the effective areas of the image. In the second row, there is no difference in color and the time is noted as 0 due to the start of the reaction. Accordingly, the intensity of red light is similar to the intensity of green light but both of them are much higher than the intensity of blue light. Therefore it is obvious that the initial color of the color reaction is close to yellow line. In the 12th row of Table 1, 20 seconds after the start of the reaction, the color reaction can be considered to stop. Comparing the intensities of the three lights at the moment, the final color of the color reaction is closer to blue. Each difference in color in Table 1 is relative to the initial color when the reaction starts. For example, the calculation of the intensity of the difference in color after 4 seconds from the reaction starts is $[(157-98)^2+(162-95)^2+(118-101)^2]^{1/2}$, and round the result off to the 2nd decimal place to get the intensity of the difference in color after 4 seconds, i.e. 90.879.

Follow the abovementioned method, measure the different samples with known but different blood sugar concentrations, implement the color analysis to measurement results, obtain the values of the differences in color of the different samples with different blood sugar concentrations at specific time after the reaction starts, and analyze the values of the differences in color and the blood sugar concentrations of those samples with the linear regression so that the relationship equation can be acquired. The relationship equation can be applied to the measurement method that calculates the blood sugar concentration through the value of the difference in color.

Figure 10:
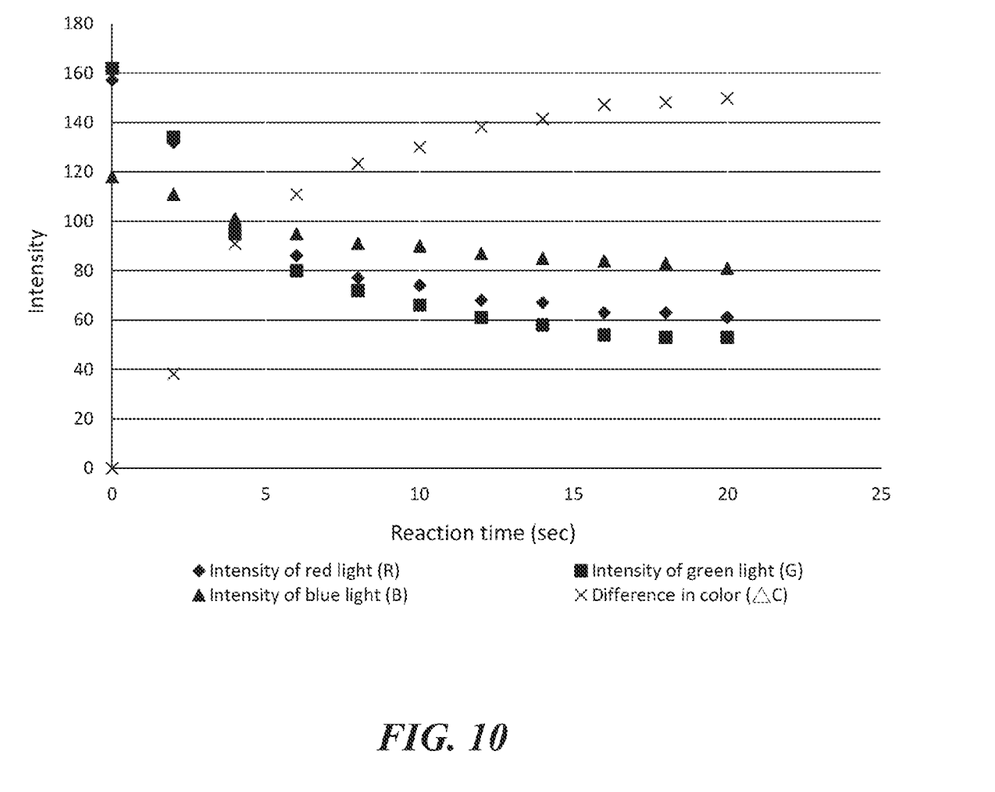
FIG. 10 is the relation plot of the attenuation of the RGB signal intensities, the increase of the intensity of the difference in color and the reaction time.

The FIG. 10 is constructed according to the data in Table 1. By FIG. 10, it is certain that the color reaction enters the stationary phase in the end. Therefore, it is proofed that the color reaction can be considered to stop after 20 seconds from the beginning. In addition, it can be observed through the present invention that the major change of the color line in the color reaction is from yellow to blue and it takes place at 4 seconds. The prior art inspector only detects the intensity change of white light, i.e. the total intensity change of the light. Thus, prior art inspector is not able to provide the user with the quantity information about the change in color line which only can be estimated by naked eyes of the user. The other prior art inspectors designed for detecting the specific color of light (i.e. specific spectrum range) is impossible to provide the user with the quantity information about the change in color line.

While the present invention has been described in connection with what is considered the most practical and preferred embodiment, it should be understood that this invention is not limited to the disclosed embodiment but is intended to cover various arrangements included within the spirit and scope of the broadest interpretation so as to encompass all such modifications and equivalent arrangements.

What is claimed is:

1. A biochemistry inspector, comprising:
an illuminant for generating a light;
a sample well for containing a sample, receiving the light and generating an image;
a photosensitive unit array configured for receiving the image and transforming the image into a pixel array; and
an image processor programmed for receiving the pixel array, transforming the pixel array into a first color space coordinate matrix, and extracting a second color space coordinate matrix from the first color space coordinate matrix according to a predetermined color space coordinate threshold.

2. The biochemistry inspector as claimed in claim 1, wherein the image processor is configured to obtains a color space vector matrix based on a predetermined color space coordinate matrix and the second color space coordinate matrix.

3. The biochemistry inspector as claimed in claim 2, wherein the image processor is configured to obtains a sample concentration matrix based on the color space vector matrix.

4. The biochemistry inspector as claimed in claim 1, wherein the illuminant is a broadband light source.

5. The biochemistry inspector as claimed in claim 1, wherein the illuminant is a white light source.

6. The biochemistry inspector as claimed in claim 1, wherein the image is composed of a transmitted light of the sample.

7. The biochemistry inspector as claimed in claim 1, wherein the image is composed of a reflected light of the sample.

8. The biochemistry inspector as claimed in claim 7, further comprising an auxiliary photodiode coupled to the image processor, wherein the auxiliary photodiode receives a transmitted light of the sample and generates an electrical signal which is received and transformed into an assistant color space coordinate scalar by the image processor.

9. The biochemistry inspector as claimed in claim 7, further comprising an auxiliary photosensitive unit array coupled to the image processor, wherein the auxiliary photosensitive unit array receives a transmitted light of the sample and generates an initial color space coordinate matrix which is received and transformed into an assistant color space coordinate matrix by the image processor.

10. A biochemistry inspector, comprising:
an illuminant for generating a light;
a sample well having a reagent for containing a sample, receiving the light and generating a first image, wherein a color reaction of the sample and the reagent is performed for a specific period of time to produce a second image;
a photosensitive unit array configured for receiving and transforming the first image and the second image into a first pixel array and a second pixel array, respectively; and
an image processor programmed for receiving and transforming the first pixel array and the second pixel array respectively into a first color space coordinate matrix and a second color space coordinate matrix, extracting a third color space coordinate matrix from the first color space coordinate matrix according to a predetermined color space coordinate threshold, extracting a fourth color space coordinate matrix from the second color space coordinate matrix according to the predetermined color space coordinate threshold, and obtaining a color space vector matrix from the third color space coordinate matrix and the fourth color space coordinate matrix.

11. The biochemistry inspector as claimed in claim 10, wherein the image processor is configured to extracts an effective color space vector matrix from the color space vector matrix according to a predetermined color space vector.

12. The biochemistry inspector as claimed in claim 10, wherein the image processor is configured to transforms the color space vector matrix into a color space scalar matrix, extracts an effective color space scalar matrix from the color space scalar matrix according to a predetermined color space scalar, and obtains an effective sample concentration matrix according to the effective color space scalar matrix.

13. A biochemistry inspection method, comprising:
obtaining a first pixel array and a second pixel array by a photosensitive unit array;

transforming the first pixel array and the second pixel array respectively into a first color space coordinate matrix and a second color space coordinate matrix;

extracting a third color space coordinate matrix and a fourth color space coordinate matrix respectively from the first color space coordinate matrix and the second color space coordinate matrix according to a predetermined color space coordinate matrix; and obtaining a color space vector matrix from the third color space coordinate matrix and the fourth color space coordinate matrix.

14. The biochemistry inspection method as claimed in claim 13, wherein the first pixel array is produced by a calibration sample image and the second pixel array is produced by a test sample image.

15. The biochemistry inspection method as claimed in claim 14, further comprising obtaining a sample concentration matrix based on the color space vector matrix.

16. The biochemistry inspection method as claimed in claim 13, wherein the first pixel array is produced by a test sample image and the second pixel array is produced by a test sample image after a predetermined period of time.

17. The biochemistry inspection method as claimed in claim 16, further comprising:

extracting an effective color space vector matrix from the color space vector matrix according to a predetermined color space vector; and obtaining an effective sample concentration matrix based on the effective color space vector matrix.

* * * * *